United States Patent [19]

Miyata et al.

[11] Patent Number: 5,110,988
[45] Date of Patent: May 5, 1992

[54] NONLINEAR OPTICAL MATERIAL

[75] Inventors: Seizo Miyata, 18-26, Shimohoya-3-chome, Hoya-shi; Takeshi Hosomi, Yokohama; Toshio Suzuki, Chigasaki; Toshiyuki Watanabe, Higashikurume; Hironobu Yamamoto; Akio Hayashi, both of Koganei, all of Japan

[73] Assignees: Sumitomo Bakelite Company Limited; Seizo Miyata; Naoya Miyata; Research Development Corporation of Japan, all of Tokyo, Japan

[21] Appl. No.: 373,131

[22] Filed: Jun. 29, 1989

[30] Foreign Application Priority Data

Aug. 23, 1988 [JP] Japan .................................. 63-208589
Sep. 2, 1988 [JP] Japan .................................. 63-219669
Nov. 30, 1988 [JP] Japan .................................. 63-303712
Nov. 30, 1988 [JP] Japan .................................. 63-303713
Mar. 20, 1989 [JP] Japan .................................. 1-68721

[51] Int. Cl.$^5$ .......................................... C07C 211/48
[52] U.S. Cl. ................................ 564/441; 252/301.16
[58] Field of Search ............................. 564/441, 443; 252/301.16

[56] References Cited

U.S. PATENT DOCUMENTS 3,920,739 11/1975 Suda et al. .......................... 564/441

OTHER PUBLICATIONS

Barluenga et al., *J. Chem. Soc. Perkin Trans. I*, 1988, vol. 7, pp. 1631-1636.
Barluenga et al., *J. Chem. Soc. Chem. Commun.*, 1983, vol. 19, pp. 1109-1110.
Braun, *Textil. Praxis*, vol. 16(8), pp. 728-733 (1961).
Houben, Chem. Ber. 41 (1908) p. 1579 (Stn Printout only).
Pedersen, J. Org. Chem. 23, pp. 255-261 (1958) (CA 52: 16280 a only).
Zinner et al., *Chem. Ber.* 94, pp. 2209-2217 (1961) (CA 55: 25914 a only).
Popp et al., Tetr. Lett. 1963 (8) p. 523 (CA 59: 5048 g only).
Lazans et al., *Chem. Abst.*, 67:64886j (1967).
Baba et al., *Chem. Abst.* 78: 28521e (1973).
Korshak et al., *Chem. Abst.* 78:110732h (1973).
Ilyushin et al., *Chem. Abs.*, 90:186506f (1979) (Stn Printout).
Le Floch et al., Bull. Soc. Chim. Fr. 1980 (3-4, Pt. 2) pp. 157-160 (CA 93: 46084d only).
Shire et al., Org. Mass Spectrum. 1981 16(4), p. 191 (CA 95:79471x only).
Xu et al., *Chem. Abs.*, 97:162500t (1982).
Yuan et al., *Chem. Abs.*, 102:24421p (1985).
Selman et al., *Chem. Abs.*, 108:5619s (1988).
Giumanini et al., J. Prakt. Chem. 1987, 329(6) pp. 1087-1103 (Chem. Abs. 110:114799n).
*Chemical Abstracts*, vol. 56, (1962) 6203g-h.
*Chemical Abstracts*, vol. 100 (1984), 102835b.
*Chemical Abstracts*, vol. 109 (1988) 128476w.
M. Barzoukas et al.: Quadratic Nonlinear Properties of N-[4-nitrophenyl]-L-prolinol and of a newly Engineered Molecular Compound N-[4-nitrophenyl]-N-methylaminoacetonitrile: a Comparative Study, vol. 4, No. 6, Jun. 1987, pp. 977-986, J. Opt. Soc. Am. B.
Patent Abstracts of Japan, vol. 12, No. 231, (P-273)[3078], Jun. 30, 1988, & JP-A-63-21627 (Toray Ind. Inc.) Jan. 29, 1988.

*Primary Examiner*—Richard L. Raymond
*Assistant Examiner*—Scott C. Rand
*Attorney, Agent, or Firm*—Browdy and Neimark

[57] ABSTRACT

A nonlinear optical material comprising a nitroaniline derivative represented by the following chemical formula:

$$A-CX_2-R$$

wherein A represents

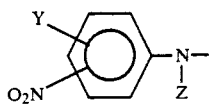

(Y represents at least one group selected from the group consisting of hydrogen, alkyl groups, deuterated alkyl groups and electron donor groups and Z represents hydrogen, deuterium, a methyl group or a deuterated methyl group), X represents hydrogen or deuterium, and R represents an alkoxy group, a deuterated alkoxy group or the same group as A.

2 Claims, No Drawings

NONLINEAR OPTICAL MATERIAL

This invention relates to an organic nonlinear optical material with large molecular hyperpolarizability $\beta$ and capable of forming noncentrosymmetric crystals.

Nonlinear optical effects refer to the phenomenon in which, when a very intense light passes through a substance, the substance is polarized by the optical field of the light. The induced polarization generates optical harmonics and the light itself undergoes change during the passing.

This phenomenon was already known before the invention of laser but cam to draw increased attention with the advent of laser beam. Clarification of phenomena such as optical harmonic generation, optical parametric oscillation and amplification, optical phase conjugation, optical bistability and the like (the application of these phenomena to optical active devices has drawn attention recently) owes much to the invention of laser. These nonlinear optical effects can find various applications such as conversion of infrared light to visible light or ultraviolet light, light amplification, light switching, optical modulation and undistorted transmission of optical signals. Nonlinear optical devices are crucial functional materials in optical information processing and optical telecommunication fields which will find increased demand in the future.

Substances showing nonlinear optical effects, such as lithium niobate ($LiNbO_3$), potassium dihydrogen phosphate (KDP), $\beta$-barium borate (BBO) and the like have been studied and some of them have been put into practical application as device material. The substances showing nonlinear optical effects, however, are not restricted to these inorganic dielectrics and are found also in organic compounds. The nonlinear optical effects of organic compounds take place owing to the movement of $\pi$ electrons delocated in the molecules, and the induced polarization in these organic compounds is far faster and larger than that in the inorganic dielectrics in which the o electrons are strongly bound by the atomic nuclei and which are restricted by their lattice vibration. In fact, 2-methyl-4-nitroaniline (hereinafter referred to as "MNA") shows a figure of merit at least 2,000 times that of lithium niobate B. F. LEVINE et al., J. Apply. Phys., Vol. 50, 2523 (1979)].

For the above reason, active researches have been carried out on organic compounds in order to realize the practical use of nonlinear optical effects, particularly optical second-harmonic generation (hereinafter referred to as "SHG") because, among the nonlinear optical effects, the second-order nonlinear optical effects are expected to find the earliest practical application as optical active device. As a result, there were proposed, as nonlinear optical materials, substances such as MNA (Japanese Patent Application Laid-Open No. 500960/1980), nitropyridine-1-oxide derivative (Japanese Patent Application Laid-Open No. 92870/1981, Japanese Patent Application Laid-Open No. 94333/1981) and the like.

In order for an organic compound to show high second-order nonlinear optical effects, the molecules must have a large dipole moment. As well known, a large dipole moment is effectively obtained by introducing an electron donor group and an electron acceptor group into a molecule.

But, even when this last requirement is satisfied, an important problem remains as the organic compound must form noncentrosymmetric crystal to exhibit second order nonlinear optical effects. And it occurs sometimes that a compound, with large molecular dipole moment, crystallizes in such arrangement that the dipole moments are cancelled as a whole. In that case, the compound has large molecular hyperpolarizability ($\beta$) but dosen't show second order nonlinear optical effect because of the centrosymmetry of the crystals or molecular aggregates. In fact, there is a lot of such organic compounds. Therefore, to develop organic material showing as essential requirement, large second order nonlinear effects, it is vitally important to synthesize compound with large molecular hyperpolarizability ($\beta$) and capable of forming crystals or molecular aggregates without centrosymmetry.

4-Nitroaniline is an aromatic compound having the simplest electron donor group and electron acceptor group and, as an organic compound, has large molecular hyperpolarizability $\beta$, but does not show second-order nonlinear optical effects. This is because the crystal forms such a molecular arrangment that the dipole moments are cancelled as a whole and therefore the crystal is centrosymmetric.

The present inventors did extensive research to improve the symmetry of 4-nitroaniline and found that some of its derivatives do not show centrosymmetry when formed into crystals or molecular aggregates. This discovery has led to the completion of the present invention.

Therefore, the object of the present invention is to provide a nonlinear optical material derived from nitroaniline, with large molecular hyperpolarizability $\beta$, capable of forming noncentrosymmetric molecular crystals of easy growth and processability.

The nonlinear optical material of the present invention for achieving the above object consists of a nitroaniline derivative represented by the following chemical formula:

wherein A represents

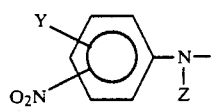

(Y represents at least one group selected from the group consisting of hydrogen, alkyl groups, deuterated alkyl groups and electron donor groups and Z represents hydrogen, deuterium, a methyl group or a deuterated methyl group), X represents hydrogen or deuterium, and R represents an alkoxy group, a deuterated alkoxy group or the same group as A.

In A, the preferable positions of substituents are such that the nitro group is at the 4-position of the phenyl group and the alkyl, deuterated alkyl or electron donor group constituting Y is at the 2-position of the phenyl group.

Examples of the alkyl group constituting Y include methyl and ethyl. Examples of the electron donor group constituting Y include methoxy and dimethylamino. The component Y is preferably methyl group, methoxy group, deuterated methyl group or deuterated methoxy group.

The nitroaniline derivative represented by the above chemical formula can be obtained, for example, by reacting the corresponding nitroaniline derivative as starting material with formaldehyde in an appropriately selected solvent at an appropriately selected pH.

Examples of the nitroaniline derivative as starting material include 4-nitroaniline, 3-nitroaniline, 2-methyl-4-nitroaniline, 2-methoxy-4-nitroaniline, 5-methyl-3-nitroaniline, N-methyl-4-nitroaniline, N-methyl-3-nitroaniline, 2-chloro-4-nitroaniline, 2-amino-5-nitropyridine, etc. These compounds are reacted with formaldehyde in a solvent of high solvency such as methanol, ethanol, methyl ethyl ketone, methyl isobutyl ketone, tetrahydrofuran, dimethylformaldehyde or the like.

When a compound of the above chemical formula wherein Y, Z and X are independently hydrogen or deuterium and R is methoxy group or deuterated methoxy group, i.e., N-methoxymethyl-4-nitroaniline, is dissolved in a solvent of high solvency such as alcohol (e.g., methanol, ethanol), a ketone (e.g., acetone, methyl ethyl ketone, methyl isobutyl ketone), tetrahydrofuran, chloroform, dichloromethane, dimethyl sulfoxide, dimethylformamide, dimethylacetamide or the like and then is crystallized in one to three days by the solvent evaporation method or the solvent cooling method, the compound can be obtained as good single crystals having sides of some millimeters.

These molecular crystals belong to the orthorhombic space group $P2_12_12_1$ and form a hexa- to tetradecahedron constituted by the planes, 101, $\bar{1}$01, 10$\bar{1}$, $\bar{1}$0$\bar{1}$, 110, $\bar{1}$10, $\bar{1}\bar{1}$0, 120, $\bar{1}$20, $\bar{1}\bar{2}$0, $\bar{1}\bar{2}$0, 010 and 0$\bar{1}$0.

The resulting nitroaniline derivative, when irradiated with an Nd:YAG laser beam ($\lambda = 1,064$ nm) in powdery state, generates second harmonics of very high intensity and green color. The nitroaniline derivative, in single crystal state, allows phase matching over a wide range and generates second harmonics of far higher intensity than that in powdery state. In general, the propagation constant of fundamental wave and that of harmonics in a crystal do not agree and accordingly, harmonics hardly appear in crystal state. The agreement of these propagation constants is called "phase matching". Unless the phase matching is attained, generation of harmonics cannot be observed. Among organic crystals, only few crystals allow phase matching. The molecular crystals according to the present invention generate second harmonics of high intensity, as mentioned above. Moreover, they allow phase matching over a wide range at the crystal growth surfaces and are superior to conventional substances in this respect, too.

When the fundamental wave is an infrared light of 1-1.2 $\mu$m, it occurs in some cases that the fundamental wave overlaps with the overtone absorption of the stretching vibration of C—H bond. Thereby the fundamental wave is absorbed and converted to thermal vibration. Therefore, when a fundamental wave of high intensity passes through crystals, the crystals cause a rise in temperature resulting in change in phase matching condition or change in angle of transmitted light. However, in the case of a particular compound of the present invention wherein the hydrogen of an alkyl group with large overtone absorption is substituted by deuterium, the absorption band is shifted to the longer wavelength side and thereby the above phenomenon can be prevented effectively.

According to the present invention, there can be provided a nonlinear optical material which is active to second-order nonlinear optical effects and has novel properties, by introducing a particular substituent at the amino nitrogen of a nitroaniline derivative which has a large dipole moment and accordingly is highly apt to form centrosymmetric crystals, or by bonding two nitroaniline derivatives with a methylene bond to reduce the symmetry of the nitroaniline derivative(s).

The present invention is explained below by means of Examples.

EXAMPLE 1

6.9 g (50 mmol) of 4-nitroaniline was dissolved in 100 ml of methanol. Thereto was added a solution obtained by diluting 10 g of 37% aqueous formaldehyde solution with 20 ml of methanol, and the resulting mixture was reacted for 3 hours at room temperature with stirring. After the completion of the reaction, the reaction mixture was concentrated. The resulting precipitate was collected by filtration, washed with 20-ml portions of methanol three times and then dried at 50° C. under reduced pressure to obtain N,N'-bis-(4-nitrophenyl)-methanediamine.

The physical properties and analytical results of the compound obtained are as follows.

Melting point: 240° C. (measured by DSC)
Molecular weight: 288 (measured by FD-MS)
Analytical results:
$^1$H-NMR (solvent: deuterated acetone): $\delta$8.05, 4H, doublet, Ar-H, $\delta$6 7.18, 2H, singlet, N-H, $\delta$6.90, 4H, doublet, Ar-H, $\delta$4.97, 2H, triplet, C-H$_2$
IR (KBr tablet): 3400 cm$^{-1}$, Ar-NH-R, 1260 cm$^{-1}$, appearance of Ar-NH-R, etc., 1620 cm$^{-1}$, disappearance of NH$_2$

EXAMPLE 2

320 mg of sodium hydroxide was dissolved in 400 ml of methanol. Thereto was added 20 g of a 37% aqueous formaldehyde solution, and the resulting mixture was reacted for 30 minutes at room temperature with stirring. Thereto was added 13.8 g of 4-nitroaniline and the resulting mixture was reacted for 6 hours at room temperature with stirring. After the completion of the reaction, the reaction mixture was poured into 2,000 ml of water and the resulting precipitate was collected by filtration.

The precipitate (reaction product) was dried under reduced pressure and then recrystallized from tetrahydrofuran to obtain N-methoxymethyl-4-nitroaniline as light yellow, transparent, stick-shaped crystals.

The physical properties and analytical results of the compound obtained are as follows.

Melting point: 115° C. (measured by DSC)
Molecular weight: 182 (measured by FD-MS)
Analytical results:
$^1$H-NMR (solvent: deuterated acetone): $\delta$8.02, 2H, doublet, Ar-H, $\delta$7.22, 1H, singlet, N-H, $\delta$6.86, 2H, doublet, Ar-H, $\delta$4.67, 2H, doublet, C-H$_2$, $\delta$3.22, 3H, singlet, C-H$_3$
IR (KBr tablet): 3330 cm$^{-1}$, Ar-NH-R, 1150, 1070 cm$^{-1}$, C-O-C, 2850 cm$^{-1}$, appearance of —OCH$_3$, etc., 1620 cm$^{-1}$, disappearance of NH$_2$

EXAMPLES 3–12

According to the above procedures, there were synthesized various nitroaniline derivatives wherein X is hydrogen and Y, Z and R each represent various groups as shown in Table 1.

Each of the nitroaniline derivatives obtained in Examples 1–12 was made of particles with diameters of 60–100 μm. These particulate samples were sandwiched between two slide glasses and irradiated with a pulse of 10 nsec using a Q-switched Nd:YAG laser ($\lambda = 1064$ nm). The intensity of the second harmonics generated from the samples was measured. The intensity of SHG (second-harmonic generation) was expressed as a relative intensity ratio when the intensity of urea was taken as 1. The results are shown in Table 1.

TABLE 1

| | Substituents of nitroaniline derivatives | | | | Position of nitro group | SHG intensity (ratio to urea powders) |
|---|---|---|---|---|---|---|
| | X | Y | Z | R | | |
| Example 1 | H | H | H | A | 4- | 120 |
| Example 2 | H | H | H | $OCH_3$ | 4- | 50 |
| Example 3 | H | 2-$CH_3$ | H | $OCH_3$ | 4- | 50 |
| Example 4 | H | 2-$CH_3O$ | H | $OCH_3$ | 4- | 20 |
| Example 5 | H | H | $CH_3$ | $OCH_3$ | 4- | 35 |
| Example 6 | H | 2-$CH_3$ | H | A | 4- | 35 |
| Example 7 | H | 2-$CH_3O$ | H | A | 4- | 10 |
| Example 8 | H | 2-$(CH_3)_2N$ | H | A | 4- | 32 |
| Example 9 | H | H | $CH_3$ | A | 4- | 10 |
| Example 10 | H | 2-$CH_3$ | $CH_3$ | A | 4- | 9 |
| Example 11 | H | 2-$CH_3O$ | $CH_3$ | A | 4- | 5 |
| Example 12 | H | 2-$CH_3$ | H | A | 5- | 26 |
| Comparative Example | | | MNA | | | 22 |

The physical properties and analytical results of the compounds obtained in Examples 3–12 are as follows.

The compound of Example 3

Melting point: 92° C. (measured by DSC)
Molecular weight: 192 (measured by FD-MS)
Analytical results:

$^1$H-NMR (solvent: deuterated DMSO): δ7.98, 1H, doublet, Ar-H, δ7.95, 1H, singlet, Ar-H, δ7.33, 1H, singlet, N-H, δ6.84, 1H, doublet, Ar-H, δ4.97, 2H, doublet, C-$H_2$, δ3.22, 3H, singlet, C-$H_3$, δ2.20, 3H, singlet, C-$H_3$ IR (KBr tablet): 3330 cm$^{-1}$, Ar-NH-R, 1150, 1070 cm$^{-1}$, C-O-C, 2850 cm$^{-1}$, appearance of —$OCH_3$, etc., 1620 cm$^{-1}$, disappearance of $NH_2$

The compound of Example 4

Melting point: 247° C. (measured by DSC)
Molecular weight: 212 (measured by FD-MS)
Analytical results $^1$H-NMR (Solvent deuterated DMSO): δ7.80, 1H, doublet, Ar-H, δ7.64, 1H, singlet, Ar-H, δ7.38, 1H, triplet, N-H, δ6.84, 1H, doublet, Ar-H, δ4.75, 2H, doublet, C-$H_2$, δ3.95, 3H, singlet, C-$H_3$, δ3.32, 3H, singlet, C-$H_3$ IR (KBr tablet): 3330 cm$^{-1}$, Ar-NH-R, 1150, 1070 cm$^{-1}$, C-O-C, 2850 cm$^{-1}$, appearance of —$OCH_3$, etc., 1620 cm$^{-1}$, disappearance of $NH_2$

The compound of Example 5

Melting point: 66° C. (measured by DSC)
Molecular weight: 196 (measured by FD-MS)
Analytical results $^1$H-NMR (solvent deuterated DMSO): δ8.06, 2H, doublet, Ar-H, δ6.95, 2H, doublet, Ar-H, δ4.9, 2H, singlet, C-$H_2$, δ3.2, 3H, singlet, C-$H_3$, δ3.1, 3H, singlet, C-$H_3$ IR (KBr tablet): 1150, 1070 cm$^{-1}$, C-O-C, 2850 cm$^{-1}$, appearance of —$OCH_3$, etc., 3330 cm$^{-1}$, disappearance of Ar-NH-R

The compound of Example 6

Melting point: 260° C. (measured by DSC)
Molecular weight: 316 (measured by FD-MS)
Analytical results $^1$H-NMR (solvent: deuterated DMSO): δ7.96, 2H, doublet, Ar-H, δ7.90, 2H, singlet, Ar-H, δ7.20, 2H, doublet, Ar-H, δ6.45, 2H, singlet, N-H, δ4.80, 2H, triplet, C-$H_2$, δ2.20, 6H, singlet, C-$H_3$ IR (KBr tablet): 3450 cm$^{-1}$, Ar-NH-R, 1260 cm$^{-1}$, appearance of Ar-NH-R, etc., 1620 cm$^{-1}$, disappearance of $NH_2$

The compound of Example 7

Melting point: 254° C. (measured by DSC)
Molecular weight: 348 (measured by FD-MS)
Analytical results $^1$H-NMR (solvent: deuterated DMSO): δ7.80, 2H, doublet, Ar-H, δ7.58, 2H, singlet, Ar-H, δ7.42, 2H, triplet, N-H, δ7.20, 2H, doublet, Ar-H, δ4.79, 2H, triplet, C-$H_2$, δ3.79, 6H, singlet, C-$H_3$ IR (KBr tablet): 3450 cm$^{-1}$, Ar-NH-R, 1260 cm$^{-1}$, appearance of Ar-NH-R, etc., 1620 cm$^{-1}$, disappearance of $NH_2$

The compound of Example 8

Melting point: 260° C. (measured by DSC)
Molecular weight: 374 (measured by FD-MS)
Analytical results $^1$H-NMR (solvent: deuterated DMSO): δ7.60, 2H, doublet, Ar-H, δ7.38, 2H, singlet, Ar-H, δ7.19, 2H, doublet, Ar-H, δ4.97, 2H, triplet, C-$H_2$ IR (KBr tablet): 3450 cm$^{-1}$, Ar-NH-R, 1260 cm$^{-1}$, appearance of Ar-NH-R, etc., 1620 cm$^{-1}$, disappearance of $NH_2$

The compound of Example 9

Melting point: 142° C. (measured by DSC)
Molecular weight: 316 (measured by FD-MS)
Analytical results $^1$H-NMR (solvent deuterated DMSO): δ8.10, 4H, doublet, Ar-H, δ6.95, 4H, doublet, Ar-H, δ5.26, 2H, triplet, C-$H_2$, δ2.98, 6H, singlet, C-$H_3$ IR (KBr tablet): 1360 cm$^{-1}$, Ar-N-R, 1250 cm$^{-1}$, appearance of Ar-N-$R_2$, etc., 1260 cm$^{-1}$, disappearance of Ar-NH-R

The compound of Example 10

Melting point: 120° C. (measured by DSC)

Molecular weight: 330 (measured by FD-MS)
Analytical results $^1$H-NMR (solvent: deuterated DMSO): δ8.01, 2H, doublet, Ar-H, δ7.95, 2H, singlet, Ar-H, δ7.25, 2H, doublet, Ar-H, δ5.36, 2H, singlet, C-H$_2$ δ2.98, 6H, singlet, C-H$_3$, δ2.22, 6H, singlet, C-H$_3$ IR (KBr tablet): 1360 cm$^{-1}$, Ar-N-R$_2$, 1250 cm$^{-1}$, appearance of Ar-N-R$_2$, etc., 1260 cm$^{-1}$, disappearance of Ar-NH-R The compound of Example 11

Melting point: 118° C. (measured by DSC)
Molecular weight: 346 (measured by FD-MS)
Analytical results $^1$H-NMR (solvent deuterated DMSO): δ7.85, 2H, doublet, Ar-H, δ7.63, 2H, singlet, Ar-H, δ7.25, 2H, doublet, Ar-H, δ5.34, 2H, singlet, C-H$_2$, δ2.98, 6H, singlet, C-H$_3$, δ3.79, 6H, singlet, C-H$_3$ IR (KBr tablet): 1360 cm$^{-1}$, Ar-N-R$_2$, 1250 cm$^{-1}$, appearance of Ar-N-R$_2$, etc., 1260 cm$^{-1}$, disappearance of Ar-NH-R The compound of Example 12

Melting point: 242° C. (measured by DSC)
Molecular weight: 316 (measured by FD-MS)
Analytical results $^1$H-NMR (solvent: deuterated DMSO): δ7.74, 2H, singlet, Ar-H, δ7.38, 2H, doublet, Ar-H, δ7.20, 2H, doublet, Ar-H, δ6.42, 2H, triplet, N-H, δ4.79, 2H, triplet, C-H$_2$, δ2.25, 6H, singlet, C-H$_3$ IR (KBr tablet): 3450 cm$^{-1}$, Ar-NH-R, 1260 cm$^{-1}$, appearance of Ar-NH-R, etc., 1620 cm$^{-1}$, disappearance of NH$_2$

EXAMPLES 13-19

Various deuterated nitroaniline derivatives were synthesized from various nitroanilines in the same procedures as in Examples 1-2 except that deuterated formaldehyde was used in place of formaldehyde and deuterated methanol was used in place of methanol.

The SHG intensity of these derivatives was measured similarly to Examples 1-12. The results are shown in Table 2 in comparison with the details of each derivative (the types of substituents X, Y, Z and R and the position of nitro group).

EXAMPLE 20

By repeating the procedures of Example 2, there was obtained N-methoxymethyl-4-nitroaniline as light yellow, transparent, stick-shaped crystals at yield of 70% and purity of 99.5%.

10 g of the N-methoxymethyl-4-nitroaniline was dissolved in tetrahydrofuran to prepare a saturated solution. The solution was subjected to the solvent evaporation method for 2 days with the temperature maintained at 25° C. to effect crystal growth, whereby the crystal growth proceeded smoothly and stick-shaped crystals of 3×5×40 mm were obtained.

EXAMPLE 21

The stick-shaped crystals (0.25×0.3×0.4 mm) of N-methoxymethyl-4-nitroaniline obtained in the same manner as in Example 20 were analyzed for crystal structure using an automatic X-ray 4-axis diffractometer.

The results are shown in Table 3.

TABLE 3

| | | | Lattice constants | | |
|---|---|---|---|---|---|
| a (Å) | b (Å) | c (Å) | α (°) | β (°) | γ (°) |
| 11.2347 | 17.5519 | 4.5708 | 90.013 | 89.977 | 89.941 |

EXAMPLE 22

The crystals of Example 21 and the crystals formed in the same manner were irradiated with a pulse of 10 nsec using a Q-switched Nd:YAG laser beam (λ=1.064 μm). As a result, by almost perpendicularly applying a fundamental wave to each of planes 110, 1$\bar{1}$0, $\bar{1}$10 and $\bar{1}\bar{1}$0, phase matching was possible and there was obtained a transmitted light of second harmonics with a far higher intensity than that (50 times urea) of the second harmonics generated in the powder state. Moreover, the acceptance-angle of phase matching was large and the phase matching was obtained easily.

Thus, the nonlinear optical material of the present invention consisting of a nitroaniline derivative, although its starting material has no or very weak SHG activity because of the centrosymmetry, shows high

TABLE 2

| | Substituents of deutreated nitroaniline derivatives | | | | Position of nitro group | SHG intensity (ratio to urea powders) |
|---|---|---|---|---|---|---|
| | X | Y | Z | R | | |
| Example 13 | D | H | D | A | 4- | 116 |
| Example 14 | D | 2-CH$_3$ | D | A | 4- | 39 |
| Example 15 | D | 2-CD$_3$ | D | A | 4- | 36 |
| Example 16 | D | 2-CD$_3$O | CD$_3$ | A | 4- | 10 |
| Example 17 | D | H | H | OCD$_3$ | 4- | 50 |
| Example 18 | D | 2-CH$_3$ | H | OCD$_3$ | 4- | 50 |
| Example 19 | D | 2-CD$_3$ | H | OCD$_3$ | 4- | 50 |

With regard to each of the compounds of Examples 13-19, it was confirmed by $^1$H-NMR that the peak of hydrogen to be substituted by deuterium had disappeared. Furthermore, according to the identification by DSC measurement and IR measurement of the compounds of Examples 13-19, it was confirmed that they respectively correspond to the deuterated nitro aniline derivatives shown in the above Table 2.

SHG efficiency as compared with urea and, depending upon the type of the nonlinear optical material, even SHG intensity higher than 100 times that of urea.

In the conventional nonlinear substances such as MNA and the like, SHG in crystal state, i.e., phase matching, is difficult. In contrast, in the optical material of the present invention, phase matching easily occurs at the grown crystal surfaces. Therefore, this is a superior property of the present optical material in molecular crystal state.

Accordingly, the optical material of the present invention can find wide applications as a material for various optical active devices (such as frequency conversion device, light control device and the like) utilizing nonlinear optical effects and electrooptic effects.

We claim:

1. A noncentrosymmetric molecular crystal of N-methoxymethyl-4-nitroniline forming a hexa- to tetradecahedron, which belongs to orthorhombic space group $p2_12_12_1$, and having plane (110) or plane (120) or a combination thereof, and which has a side of at least 0.25 mm.

2. A noncentrosymmetric molecular crystal according to claim 1, wherein at least one of the hydrogen atoms in N-methoxymethyl-4-nitroaniline is a deuterium atom.

* * * * *